United States Patent [19]

Matsutani et al.

[11] Patent Number: 4,955,898
[45] Date of Patent: Sep. 11, 1990

[54] SURGICAL STAPLE

[75] Inventors: Kanji Matsutani, Tochigi; Masatoshi Fukuda, Utsunomiya, both of Japan

[73] Assignee: Matsutani Seisakusho Co., Ltd., Tochigi, Japan

[21] Appl. No.: 429,079

[22] Filed: Oct. 30, 1989

[30] Foreign Application Priority Data

Oct. 31, 1988 [JP] Japan ............... 63-275249

[51] Int. Cl.$^5$ ........................... A61B 17/00
[52] U.S. Cl. .................. 606/219; 411/457; 411/471; 227/902
[58] Field of Search ............. 606/219; 411/457, 471; 227/19, 902

[56] References Cited

U.S. PATENT DOCUMENTS

| | | | |
|---|---|---|---|
| 3,583,663 | 6/1971 | Snow | 411/457 |
| 4,014,492 | 3/1977 | Rothfuss | 606/219 |
| 4,131,975 | 1/1979 | Niedecker | 411/457 |
| 4,505,273 | 3/1985 | Braun et al. | 606/219 |
| 4,610,251 | 9/1986 | Kumar | 606/219 |
| 4,669,647 | 6/1987 | Storace | 606/219 |

FOREIGN PATENT DOCUMENTS

| | | | |
|---|---|---|---|
| 944305 | 6/1956 | Fed. Rep. of Germany | 411/457 |
| 1005249 | 12/1951 | France | 411/457 |
| 484793 | 9/1953 | Italy | 411/471 |
| 57-46854 | 10/1982 | Japan. | |
| 61-4535 | 2/1986 | Japan. | |
| 62-36694 | 8/1987 | Japan. | |
| 62-37983 | 8/1987 | Japan. | |
| 1311721 | 5/1987 | U.S.S.R. | 128/335 |

Primary Examiner—Randall L. Green
Assistant Examiner—Gary Jackson
Attorney, Agent, or Firm—Wegner & Bretschneider

[57] ABSTRACT

A surgical staple has a base portion and a pair of leg portions respectively extending angularly from the opposite ends of the base portion. Each leg portion has at its distal end portion a first inclined surface and a second inclined surface extending from the first inclined surface to the distal end of said leg portion. The first and second inclined surfaces are inclined with respect to the axis of the leg portion. The angle between the first inclined surface and the axis of the leg portion is smaller than the angle between the second inclined surface and the axis of the leg portion. The second inclined surface terminates in a sharp edge at its distal end. For producing the surgical staple, a blade is moved toward each of the leg portions in inclined relation to the axis thereof to shear the leg portion, so that a smooth sheared surface and a coarse ruptured surface are formed on the distal end portion of the leg portion and arranged in this order toward the distal end of the leg portion. The sheared surface defines the first inclined surface whereas the ruptured surface defines the second inclined surface. A shearing member having the above blade serves to bend and shear the leg portions of the surgical staple.

4 Claims, 6 Drawing Sheets

SURGICAL STAPLE

BACKGROUND OF THE INVENTION

1. Field of the Invention

This invention relates to a surgical staple and a method of and apparatus for producing such a surgical staple.

2. Prior Art

A conventional surgical staple comprises a steel wire of a circular cross-section, and has a base portion and a pair of leg portions respectively extending angularly from the opposite ends of the base portion, the distal end of each leg portion being sharp. A number of such staples are adapted to be loaded into a stapler. The stapler is operated to bend the base portion at two points disposed respectively adjacent to the pair of leg portions, so that the pair of leg portions are driven into the body of the patient on opposite sides of a wound, and at the same time are urged toward each other, thereby suturing or sewing up the wound.

There are known various types of staples. A first type of staple, as shown in FIG. 19 of Japanese Patent Publication No. 36694/87, has a straight base portion and a pair of parallel leg portions respectively extending perpendicularly from the opposite ends of the base portion. A second type of staple, as shown in FIG. 12 of Japanese Patent Publication No. 46854/82, is similar to the first type of staple, but differs in that the central portion of its base portion is bent in a direction of extending of its leg portions. A third type of staple, as shown in FIG. 31 of Japanese Patent Publication No. 37983/87, has a base portion which is so bent that the overall shape of the staple is much like a figure "3", and its leg portions are not parallel to each other but are directed outwardly away from each other. A fourth type of staple, as shown in FIG. 5 of Japanese Patent Publication No. 4535/86, is similar to the third type of staple but has a pair of leg portions directed inwardly toward each other.

In each of the above four types of staples, the axis of the base portion and the axes of the pair of leg portions are disposed in a common plane. Further, each of the leg portions has at its distal end portion only one inclined surface inclined with respect to the axis of the leg portion. This inclined surface perpendicularly intersects the above common plane, and faces outwardly, that is, away from the opposite leg portion. The inclined surface intersects the cylindrical peripheral surface of the leg portion at the distal end thereof to form a sharp edge.

The above conventional staples has a drawback. More specifically, each leg portion of the staple has the sole inclined surface, and the angle of the distal end edge is equal to the angle between the axis of the leg portion and the inclined surface. When the angle of the distal end edge is made smaller, the ability of the leg portion to penetrate into the human body is enhanced, but the strength of the distal end edge decreases. In contrast, when the angle of the distal end edge is made larger, its strength is increased, but the penetrating ability thereof decreases. Thus, it has been difficult to enhance both of them.

The inventor of the present invention has magnified and observed the inclined surface from the side thereof, with the leg portion held in a vertical condition, and has found that one of about right and left halves of the inclined surface is relatively smooth whereas the other is coarse. The present inventor has presumed from this fact that in the conventional staples, the inclined surface is formed in the following manner: Cutting edges of upper and lower blade members are disposed in parallel relation to the above common plane in which the axis of the base portion of the staple as well as the axes of the pair of leg portions is disposed, and the cutting edge of the upper blade member is moved in a direction perpendicular to the above common plane to shear each leg portion to thereby form the inclined surface. As a result, one of the right and left halves of the inclined surface defines a relatively smooth sheared surface whereas the other defines a coarse ruptured surface. With this shearing method, the staple suffers from the following drawbacks in addition to the above-mentioned drawback:

(1) When the leg portion of the staple held in a vertical condition is viewed from the side thereof, the axis of the leg portion is bent to either the right or the left in the vicinity of the distal end of the leg portion. It is thought that this arises out of the fact that the leg portion is deformed in the vicinity of its distal end when the upper blade member is moved to effect the shearing. Because of such bending of the distal end portion of the leg portion, the leg portion has a lowered penetrating ability.

(2) When the distal end edge of the leg portion in which the inclined surface terminates has been magnified and observed in a direction perpendicular to the above plane, the distal end edge assumes a relatively rounded configuration. It is thought that this arises out of the fact that the distal end edge is curled on the upper blade member when the leg portion is sheared. This results in a lowered penetrating ability of the leg portion.

(3) Burrs are formed on the side edge of the leg portion defined by the ruptured surface (defining one of the right and left halves of the inclined surface) and the cylindrical peripheral surface of the leg portion. These burrs damage the flesh of the patient when the leg portion is caused to penetrate thereinto.

SUMMARY OF THE INVENTION

It is therefore an object of this invention to provide a surgical staple in which the distal end portions of the leg portions have a high strength, and the leg portions have a satisfactory penetrating ability.

According to a first aspect of the present invention, there is provided a surgical staple comprising a body having an elongated base portion and a pair of leg portions extending respectively from opposite ends of the base portion in intersecting relation to the base portion, each of the leg portions having a pair of first and second inclined surfaces at an outer periphery of a distal end portion of the leg portion remote from the base portion, the first and second inclined surfaces being inclined with respect to the axis of the leg portion, the first inclined surface being disposed intermediate the opposite ends of the leg portion, the second inclined surface extending between the first inclined surface and the distal end of the leg portion, the angle of the first inclined surface with respect to the axis of the leg portion being smaller than the angle of the second inclined surface with respect to the axis of the leg portion, the second inclined surface intersecting the outer peripheral surface of the leg portion at the distal end of the leg portion to form a sharp distal end edge.

According to a second aspect of the invention, there is provided a method of producing a surgical staple, comprising the steps of:

(a) bending opposite end portions of a wire in intersecting relation to a central portion of the wire lying between the opposite end portions of the wire; the central portion defining a base portion of the staple; and (b) moving a blade of shearing means toward each of the opposite end portions of the wire in inclined relation to the axis of the end portion to shear the end portion to provide a staple body, so that a smooth sheared surface and a coarse ruptured surface are formed on each of opposite end portions of the staple body and arranged in this order toward the end of the staple body, the opposite end portions of the staple body respectively defining a pair of leg portions of the staple extending respectively from the opposite ends of the base portion, the sheared surface and the ruptured surface respectively defining a first inclined surface and a second inclined surface, the first and second inclined surfaces being inclined with respect to the axis of the leg portion, the angle of the first inclined surface with respect to the axis of the leg portion being smaller than the angle of the second inclined surface with respect to the axis of the leg portion, the second inclined surface intersecting the outer peripheral surface of the leg portion to form a sharp end edge.

According to a third aspect of the invention, there is provided an apparatus for producing a surgical staple, comprising:

(a) a fixed bed having a support surface for supporting a wire of a predetermined length thereon;

(b) a holder member movable in a direction substantially perpendicular to the support surface so as to hold a central portion of the wire between the holder member and the support surface;

(c) shearing means disposed in opposed relation to the support surface and having a pair of opposed first projections each extending in a direction perpendicular to the plane of the support surface, the pair of first projections having their respective inner surfaces facing each other, each the inner surface having a step portion intermediate opposite ends thereof, the inner surface of each first projection terminating in an inner cutting edge at its distal end, the shearing means being movable in a direction perpendicular to the plane of the support surface between a first position where the shearing means is spaced apart from the fixed bed and a second position where the fixed bed is received between the pair of first projections, the inner cutting edge extending in a direction subsequently perpendicular to the direction of movement of the shearing means; and (d) receptive means disposed on that side of the fixed bed disposed opposite to the shearing means, the receptive means having a pair of opposed second projections, the pair of second projections having their respective slanting surfaces at their outer sides facing away from each other, the slanting surfaces being inclined at a predetermined angle with respect to the direction of movement of the shearing means and converging toward the fixed bed, the receptive means being movable in a direction perpendicular to the plane of the support surface between an inoperative position where the receptive means is spaced apart from the fixed bed and an operative position where the fixed bed is received between the pair of second projections;

(e) whereby when the shearing means moves from the first position toward the second position, with the central portion of the wire held between the support surface and the holder member, the opposite end portions of the wire respectively extending outwardly from the opposite ends of the fixed bed are urged by the pair of first projections to be bent into engagement respectively with the slanting surfaces of the receptive means held in the operative position, so that the thus bent opposite end portions of the wire respectively define a pair of leg portions of a staple body whereas the central portion of the wire defines a base portion of the staple body, the angle between the leg portion and the base portion being generally equal to the angle between the support surface and the slanting surface; when the shearing means further moves toward the second position with the receptive means remaining in the operative position, the inner cutting edges of the shearing means respectively shear the distal end sections of the pair of leg portions, so that a smooth sheared surface and a coarse ruptured surface are formed on each of the leg portions and arranged in this order toward the distal end of the leg portion, the sheared surface defining a first inclined surface, the angle of the first inclined surface with respect to the axis of the leg portion being generally equal to the angle of the slanting surface with respect to the direction of movement of the shearing means, the ruptured surface defining a second inclined surface, the angle between the second inclined surface and the axis of the leg portion being greater than the angle between the first inclined surface and the axis of the leg portion, the second inclined surface intersecting the outer peripheral surface of the leg portion to form a sharp end edge, and when the shearing means further moves to the second position with the receptive means moving toward the inoperative position, the step portion being brought into contact with the leg portion and urges the leg portion toward the opposite leg portion, so that the leg portion is bent at an angle of substantially 90° with respect to the base portion.

DESCRIPTION OF THE PREFERRED EMBODIMENT OF THE INVENTION

The invention will now be described with reference to the drawings.

Figure 1:
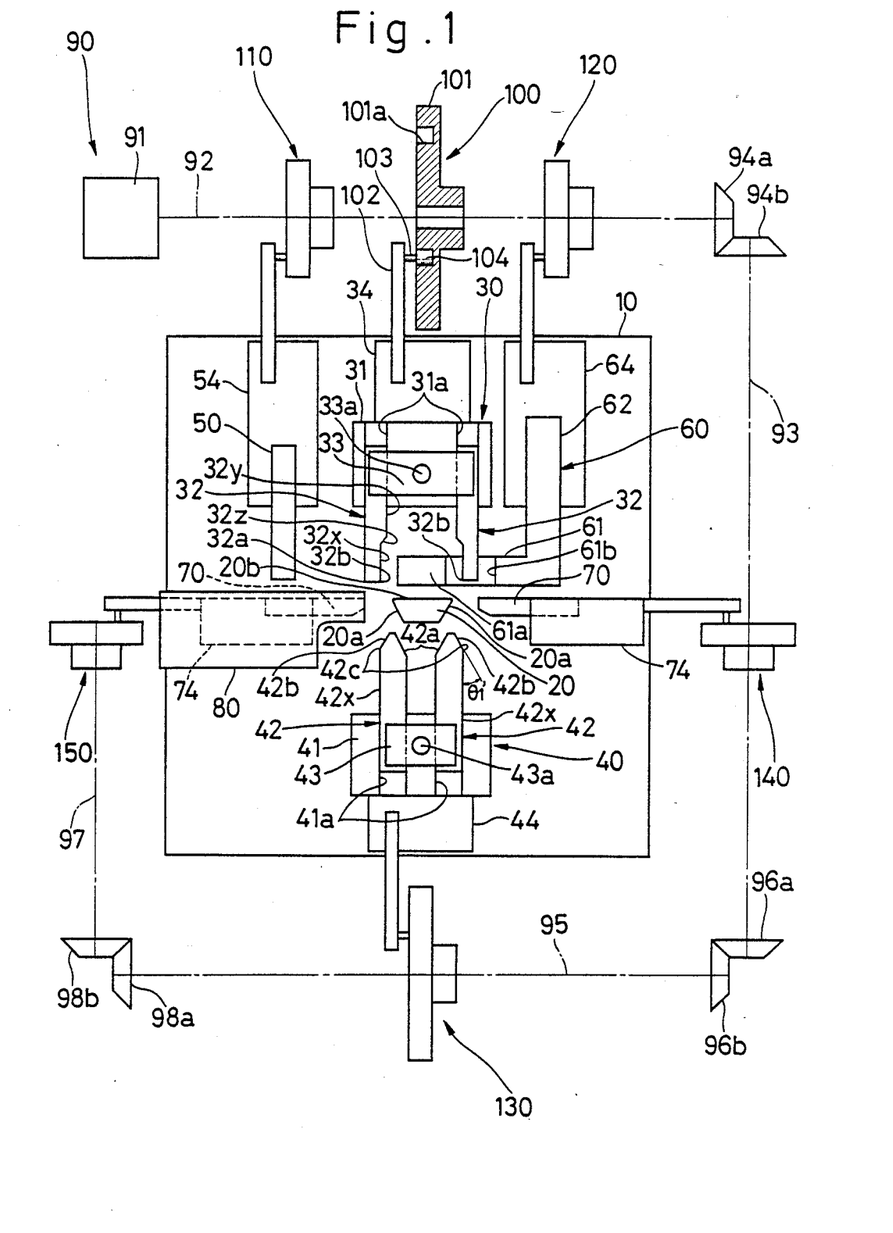
FIG. 1 is a front-elevational view of a staple producing apparatus provided in accordance with the present invention.
Figure 2:
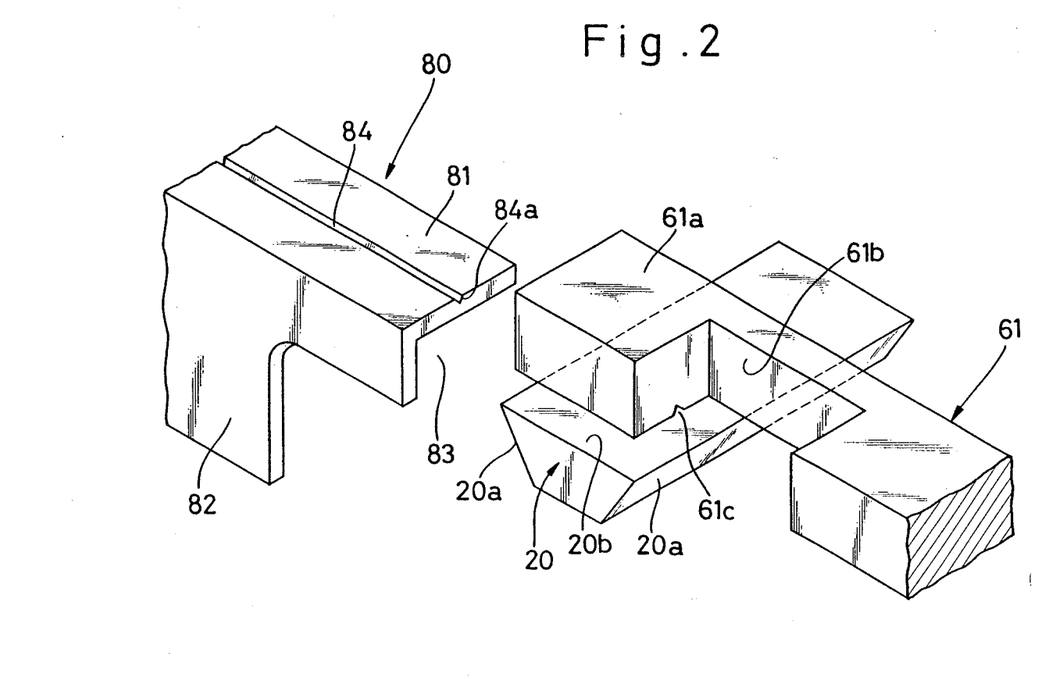
FIG. 2 is a perspective view of a portion of the apparatus, showing a fixed bed, a receptive member and a second holder member.

FIGS. 1 and 2 show an apparatus for producing a surgical staple. The apparatus includes a rear plate 10 which is disposed vertically and is disposed parallel to the sheet of FIG. 1. An elongated fixed bed 20 extends horizontally through a central portion of the rear plate 10 in perpendicular relation thereto, and is fixed to the rear plate 10. The fixed bed 20 has an inverted trapezoidal cross-section, and has a pair of inclined opposite sides or surfaces 20a and 20a. A top surface 20b of the fixed bed 20 is flat and serves as a support surface.

A shearing assembly 30 is mounted above the fixed bed 20, and a receptive assembly 40 is mounted below the fixed bed 20. A first holder member 50 is provided on the left side of the shearing assembly 30, and a second holder member 60 is provided on the right side of the shearing assembly 30. A pair of third holder members 70 and 70 are provided respectively on the opposite sides of the fixed bed 20. A lower blade member 80 is provided on the left side of the fixed bed 20.

The shearing assembly 30 includes a holder 31 having a pair of vertical grooves 31a and 31a. A pair of blade members 32 and 32 of an identical shape are respectively received at their upper end portions in the pair of vertical grooves 31a and 31a. Each blade member 32 extends downwardly beyond the holder 31, and has a rectangular transverse cross-section. A clamp plate 33 is fastened to the holder 31 by a screw 33a to press the upper end portions of the blade members 32 and 32 against the holder 31 to thereby fix these blade members to the holder 31. The lower end face of each blade member 32 is flat and is disposed horizontally. The outer and inner side edges of this lower end face serve as straight cutting edges 32a and 32b, respectively. The cutting edges 32a and 32b extend horizontally in perpendicular relation to the rear plate 10. Actually, the outer cutting edge 32a of the right-hand blade member 32 is not used.

The inner surface of the blade member 32 extends vertically. This inner surface has upper and lower flat vertical portions 32y and 32x disposed perpendicularly to the rear plate 10, and an inclined step portion 32z interconnecting the upper and lower portions 32y and 32x. The upper portion 32y is offset from the lower portion 32x toward the opposite blade member 32. The lower portion 32x terminates at its lower end in the cutting edge 32b. Because of the provision of the step portions 32z and 32z, the distance between the opposed upper portions 32y and 32y of the inner surfaces of the two blade members 32 and 32 is smaller than the distance between the opposed lower portions 32x and 32x.

The holder 31 of the shearing assembly 30 is fixedly secured to a slider 34, and the slider 34 is supported by a guide member (not shown), mounted on the rear plate 10, so as to move vertically, that is, upward and downward.

The receptive assembly 40 includes a holder 41 which has a pair of vertical grooves 41a and 41a. A pair of receptive members 42 and 42 of an identical shape are respectively received at their lower end portions in the pair of vertical grooves 41a and 41a. Each receptive member 42 has a rectangular cross-section, and extends upwardly beyond the holder 41. A clamp plate 43 is fastened to the holder 41 by a screw 43a to press the lower end portions of the receptive members 42 and 42 against the holder 41 to thereby fix these receptive members to the holder 41.

The opposite inner and outer surfaces of the upper end portion of each receptive member 42 are inclined to provide a pair of slanting surfaces 42a and 42b converging toward the upper end of the receptive member 42. The angle of the inner slanting surface 42a with respect to a vertical plane perpendicular to the rear plate 10 is substantially equal to the inclined angle of the inclined surface 20a of the fixed bed 20. The angle $\theta 1'$ of the outer slanting surface 42b with respect to the above vertical plane is preferably between 22° to 32°, and for example, 30°.

The receptive member 42 has a flat outer surface 42x disposed perpendicular to the rear plate 10. The outer inclined surface 42b intersects the outer surface 42x to form an edge 42c which is straight and horizontally extends perpendicularly to the rear plate 10.

The holder 41 of the receptive assembly 40 is fixedly secured to a slider 44, and the slider 44 is supported by a guide member (not shown), mounted on the rear plate 10, so as to move vertically, that is, upward and downward.

The first holder member 50 extends vertically, and is fixedly secured at its upper end portion to a slider 54. The slider 54 is supported by a guide member (not shown), mounted on the rear plate 10, so as to move vertically, that is, upward and downward.

The second holder member 60 is of an L-shape, and has a vertical portion 62 and a horizontal portion 61 extending perpendicularly from the lower end of the vertical portion 62 in a left-hand direction (FIG. 1). A distal end portion 61a of the horizontal portion 61 is disposed just above the fixed bed 20. As shown in FIG. 2, a support groove 61c is formed in the lower surface of the distal end portion 61a, and extends horizontally in parallel relation to the rear plate 10. A notch or opening 61b is formed through the horizontal portion 61 intermediate the opposite ends thereof, the notch 61b being open to one side surface of the horizontal portion 61 facing away from the rear plate 10. The right-hand blade member 32 of the shearing assembly 30 is receivable in the notch 61b. The vertical portion 62 is fixedly secured at its upper end portion to a slider 64. The slider 64 is supported by a guide member (not shown), mounted on the rear plate 10, so as to move vertically, that is, upward and downward.

The pair of third holder members 70 and 70 extend horizontally, and their one ends are respectively disposed in opposed relation to the opposite sides of the fixed bed 20 whereas the other ends are fixedly secured to sliders 74 and 74, respectively. Each of the sliders 74 is supported by a guide member (not shown), mounted on the rear plate 10, so as to move horizontally, that is, in the right-hand and left-hand directions (FIG. 1).

As shown in FIG. 2, the lower blade member 80 has an L-shaped cross-section, and has a horizontal plate portion 81 and a vertical plate portion 82. The horizontal plate portion 81 is fixedly secured at one side edge to the rear plate 10, and the vertical plate portion 82 extends downwardly from the other side edge of the horizontal plate portion 81 and is disposed in parallel spaced relation to the rear plate 10. An accommodation space 83 is formed between the rear plate 10 and the vertical plate portion 82, and the left-hand third holder member 70 as well as the slider 74 associated therewith is received in the accommodation space 83. A guide groove 84 is formed in the upper surface of the horizontal plate portion 81, and extends in parallel relation to the rear plate 10. An end edge 84a of the guide groove 84, provided on one end face of the horizontal plate portion 81 facing the fixed bed 20, serves as a cutting edge.

The staple producing apparatus further comprises a drive system 90 including a motor 91. A first shaft 92 extending horizontally is connected at its left-hand end to the motor 91, and a second shaft 93 extending vertically is connected at its upper end to the right-hand end of the first shaft 92 through bevel gears 94a and 94b. A third shaft 95 extending horizontally is connected at its right-hand end to the lower end of the second shaft 93 through bevel gears 96a and 96b. A fourth shaft 97 extending vertically is connected at its lower end to the left-hand end of the third shaft 95 through bevel gears 98a and 98b. The four shafts 92, 93, 95 and 97 are rotatably supported by bearing members (not shown).

The slider 34 supporting the shearing assembly 30 is connected to the first shaft 92 through a cam mechanism 100. The cam mechanism 100 will now be described. A disc-shaped cam 101 is fixedly mounted on the first shaft 92 for rotation therewith, the cam 101 having a cam groove 101a formed in its left side thereof. A vertical link 102 is connected at its lower end to the slider 34. A roller 104 serving as a cam follower is rotatably mounted on the upper end of the link 102 by a pin 103, the roller 104 being received in the cam groove 101a for movement therealong. The rotation of the cam 101 caused by the rotation of the first shaft 92 is transmitted to the slider 34 via the roller 104, the pin 103 and the link 102. With this arrangement, when the first shaft 92 makes one rotation, the shearing assembly 30 makes one vertical reciprocal movement, that is, moves downward and upward.

Similarly, one rotation of the first shaft 92 is converted into one vertical reciprocal movement of the first holder member 50 via a cam mechanism 110, and also one rotation of the first shaft 92 is converted into one vertical reciprocal movement of the second holder member 60 via a cam mechanism 120. One rotation of the third shaft 95 is converted into one vertical reciprocal movement of the receptive assembly 40 via a cam mechanism 130. One rotation of the second shaft 93 is converted into one horizontal reciprocal movement of the right-hand third holder member 70 via a cam mechanism 140, and one rotation of the fourth shaft 97 is converted into one horizontal reciprocal movement of the left-hand third holder member 70 via a cam mechanism 150. The construction of the cam mechanisms 110, 120, 130, 140 and 150 is the same as that of the cam mechanism 100, and therefore will not be described here.

A method of producing the surgical staple using the above-mentioned apparatus will now be described with reference to FIGS. 3 to 9. In FIGS. 3 to 8, some of the component parts are omitted or shown schematically, and the diameter of a steel wire 1A is shown in an exaggerated manner.

Figure 3:
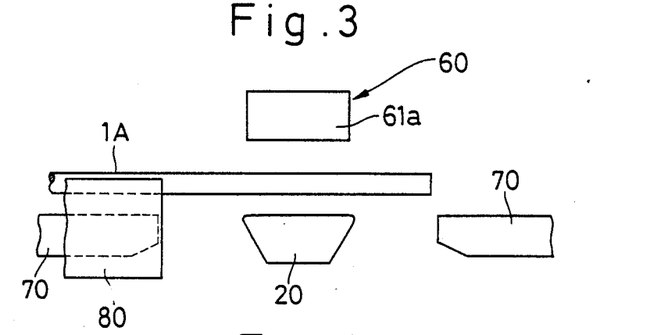
FIGS. 3 to 9 are views illustrative of the sequence of a staple-producing operation.

As shown in FIG. 3, the steel wire 1A of a circular cross-section is guided by the guide groove 84 of the lower blade member 80 and is intermittently fed a predetermined amount by a feed means (not shown) in the right-hand direction, the feed means being provided on the left side of the first holder member 50. Before the steel wire 1A is fed, the leading end of the steel wire 1A is positioned at the cutting edge 84a defined by the end edge of the guide groove 84 in the lower blade member 80. When the steel wire 1A is fed, it moves beyond the lower blade member 80 in the right-hand direction, and passes past a position above the fixed bed 20 into an operative position. When the steel wire 1A is fed the predetermined amount to the operative position, the fixed bed 20 is disposed beneath a central section of that portion (hereinafter referred to as "projecting portion") of the steel wire 1A projecting from the lower blade member 80, as shown in FIG. 3. In this condition, the shearing assembly 30, the receptive assembly 40 and the holder members 50, 60, 70 and 70 are disposed at their respective retracted or inoperative positions shown in FIG. 1.

Figure 4:
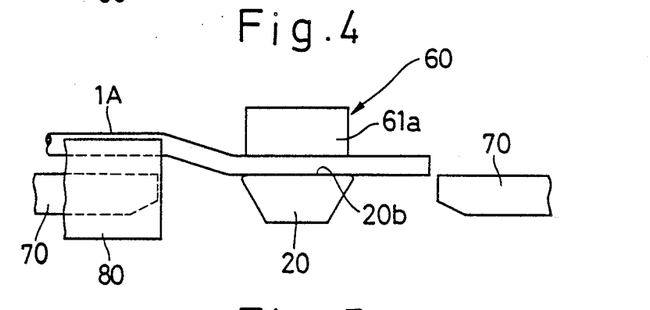

Then, the first holder member 50 moves downward to hold the steel wire 1A, received in the guide groove 84, against movement, and at the same time the second holder member 60 moves downward, so that its distal end portion 61a presses the central section of the projecting portion (leading end portion) of the steel wire 1A against the support surface 20b of the fixed bed 20, as shown in FIG. 4. As a result, the projecting portion of the steel wire A is received in the support groove 61c of the second holder member 60 and is therefore prevented from lateral movement. The level or height of the projecting portion of the steel wire 1A held against the fixed bed 20 is lower than the level of that portion of the steel wire 1A, held by the lower blade member 80, by an amount, for example, equal to the diameter of the steel wire 1A.

Figure 5:
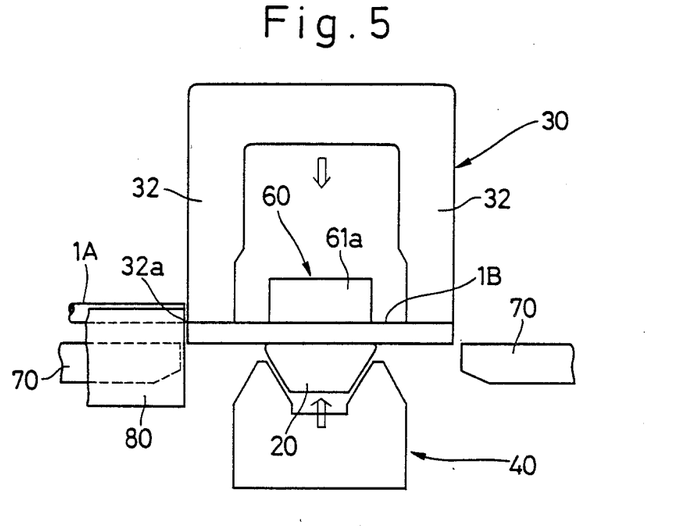

Then, as shown in FIG. 5, the shearing assembly moves 30 downward, and at the same time the receptive assembly 40 moves upward. When the shearing assembly 30 moves downward, the outer cutting edge 32a of the left-hand blade member 32 cooperates with the cutting edge 84a on the right-hand end of the lower blade member 80 to shear the steel wire 1A, thus providing a length of steel wire 1B corresponding to the above-mentioned predetermined feed of the steel wire 1A. The steel wire 1B is held or clamped at its central portion between the fixed bed 20 and the distal end portion 61a of the second holder member 60, with the opposite end portions thereof disposed in a floating condition.

Figure 6:
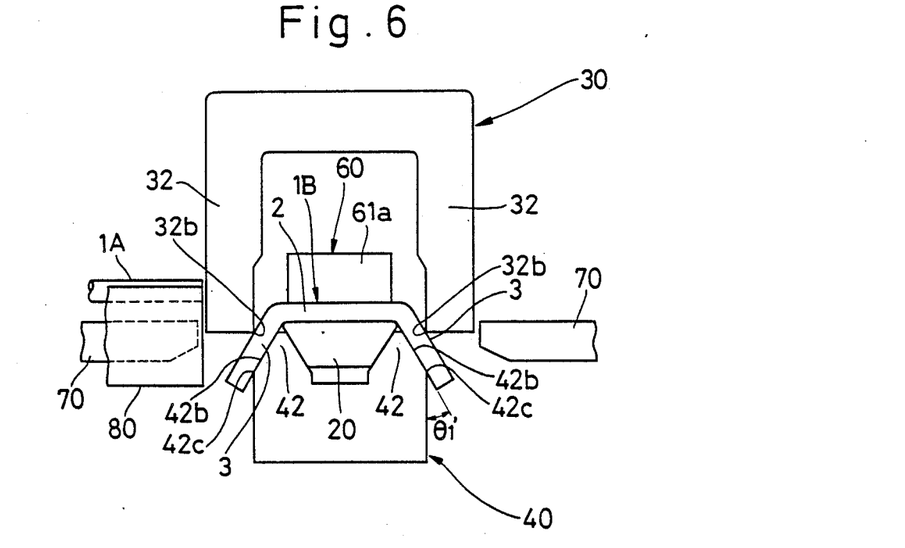

Immediately after the above shearing of the steel wire 1A, the pair of receptive members 42 and 42 of the receptive assembly 40 are brought into contact with the fixed bed 20, as shown in FIG. 6. The receptive assembly 40 is maintained at this operative position for a predetermined length of time. In this condition, the slanting surface 42b of the right-hand receptive member 40 is disposed in a plane in which the right side edge of the support surface 20b of the fixed bed 20 lies, and also the slanting surface 42b of the left-hand receptive member 40 is disposed in a plane in which the left side edge of the support surface 20b lies.

After the above-mentioned shearing of the steel wire 1A, the shearing assembly 30 further moves downward, and as shown in FIG. 6, the inner cutting edges 32b and 32b of the two blade members 32 and 32 urge and bend the opposite end portions of the steel wire 1B downwardly. Such bending position is determined by the opposite (right and left) side edges of the support surface 20b of the fixed bed 20. The opposite end portions of the steel wire 1B are bent until they are brought into contact with the slanting surfaces 42b and 42b of the two receptive members 42 and 42, respectively. As a result, the straight central portion of the steel wire 1B serves as a base portion 2 of the staple body, and its opposite end portions serve as a pair of leg portions 3 and 3, respectively. The angle between each leg portion 3 and the base portion 2 is equal to the angle $(90-\theta')$ between the support surface 20b of the fixed bed 20 and the slanting surface 42b of the receptive member 42.

Figure 7:
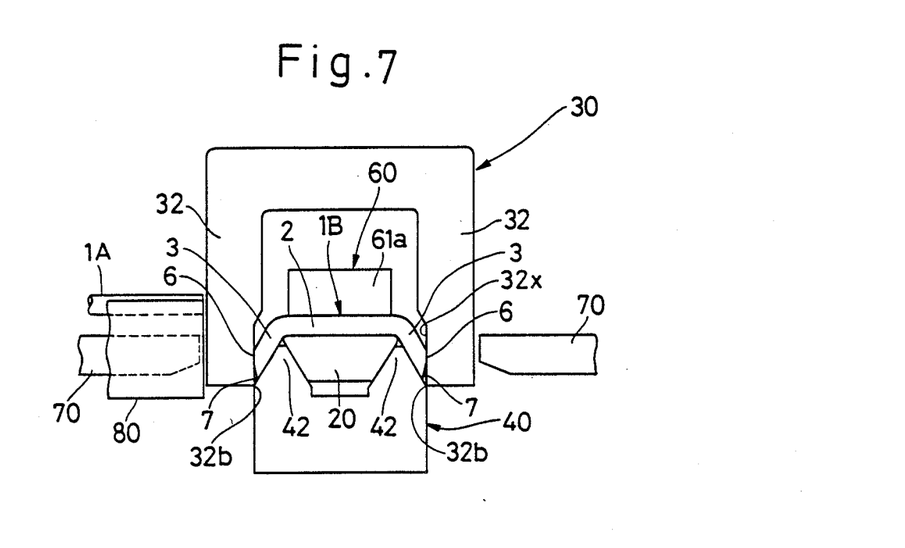

After the above bending operation, the receptive assembly 40 remains stationary, and the shearing assembly 30 further moves downward. As a result, as shown in FIG. 7, the inner cutting edges 32b and 32b of the two blade members 32 and 32 cooperates respectively with the edges 42c and 42c of the two receptive members 42 and 42 to shear the distal ends of the leg portions 3 and 3. The direction of this shearing is inclined with respect to the axis of the leg 3 at an angle equal to the angle $\theta 1'$ between the slanting surface 42b of the receptive member 42 and a vertical line. Until about midway through the shearing, the leg portion 3 is cut by the cutting edge 32b, and the cutting edge 32b and the lower portion 32x of the inner surface of the blade member 32 move relative to the sheared surface in close contact therewith, so that the sheared surface designated at 6 is made smooth. Subsequently, the distal end of the leg portion 3 is ruptured or torn off to form a ruptured surface 7 which is coarser than the sheared surface 6. The sheared surface 6 and the ruptured surface 7, disposed in this order toward the distal end of the leg portion 3, are continuous with each other, and are generally flat. The angle of the sheared surface 6 with respect to the axis of the leg portion 3 is generally equal to the aforesaid angle $\theta 1'$, and actually is slightly smaller than the angle $\theta 1'$, for example, by about 2°. The angle of the ruptured surface 7 with respect to the axis of the leg portion 3 is larger than the angle between the sheared surface 6 and the axis of the leg portion 3. The sheared surface 6 defines a first inclined surface, and the ruptured surface 7 defines a second inclined surface.

Figure 8:
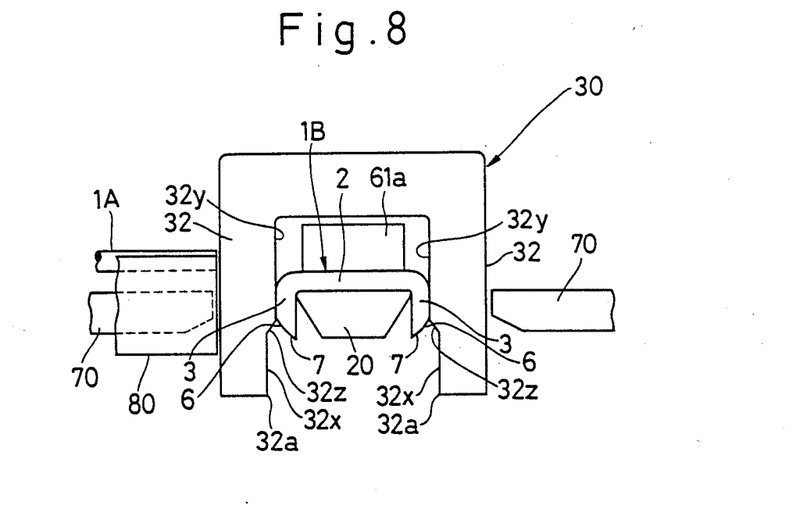

Thereafter, as shown in FIG. 8, the receptive assembly 40 moves downward into its retracted position, and the shearing assembly 30 further moves downward. When the shearing assembly 30 moves downward, the inclined step portion 32z of the inner surface of the blade member 32 is brought into engagement with the leg portion 3, so that the leg portion 3 is bent in such a manner that the leg portion 3 is disposed at an angle of substantially 90° with respect to the base portion 2. Subsequently, the leg portion 3 is held in contact with the upper portion 32y of the inner surface of the blade member 32 and is maintained in its right-angularly bent condition.

Figure 9:
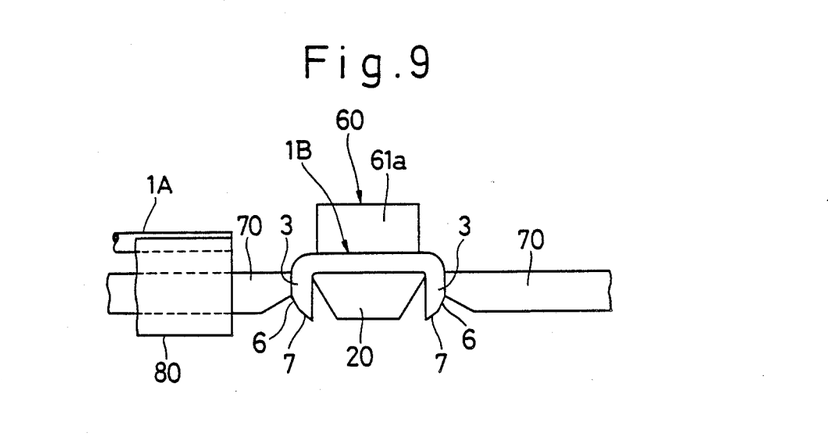
Figure 10:
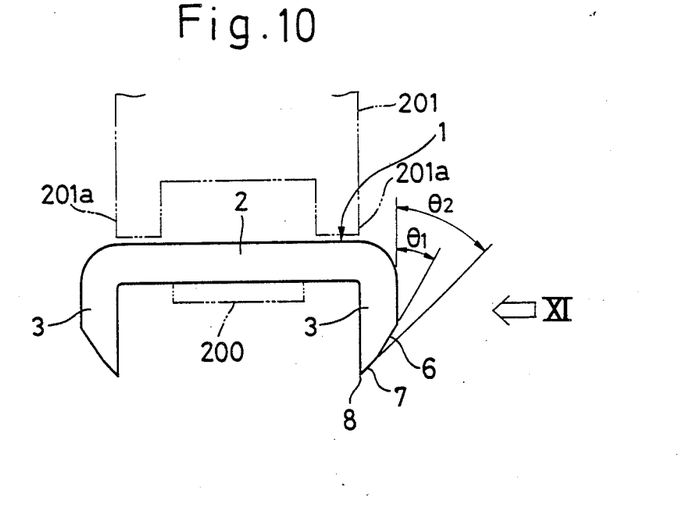
FIG. 10 is a front-elevational view of the staple.

Then, the shearing assembly 30 moves upward to its retracted position, and as shown in FIG. 9, the pair of third holder members 70 and 70 are brought into engagement with the pair of leg portions 3 and 3, respectively, so that the leg portions 3 and 3, which are slightly moved away from each other because of its slight resilient nature upon disengagement of the shearing assembly 30 from the steel wire 1B, are bend accurately right-angularly (90°) with respect to the base portion 2, thus providing the surgical staple 1 shown in FIG. 10. Then, the pair of third holder members 70 and 70 are moved away from the fixed bed 20 into their respective retracted positions, thus completing the steps of producing the surgical staple 1.

Figure 11:
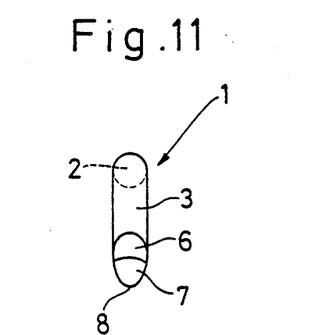
FIG. 11 is a side-elevational view of the staple as viewed in a direction of arrow XI of FIG. 10.

The thus completed surgical staple 1 will now be described with reference to FIGS. 10 and 11 in which the diameter of the surgical staple 1 is shown in an exaggerated manner. As described above, the surgical staple 1 comprises the steel wire of a circular cross-section, and has the straight base portion 2 and the pair of parallel opposed, straight leg portions 3 and 3 respectively extending perpendicularly from the opposite ends of the base portion 2. The axis of the base portion 2 and the axes of the leg portions 3 and 3 are disposed in a common plane.

Each leg portion 3 has, at the outer surface of its distal end portion facing away from the opposite leg portion 3, the first inclined surface 6 and the second inclined surface 7 extending between the first inclined surface 6 and the distal end or edge of the leg portion 3. The two inclined surfaces 6 and 7 are disposed perpendicularly to the above common plane. The angle $\theta 1$ between the first inclined surface 6 and the axis of the leg portion 3 is preferably in the range of between 20° and 30°, and for example, 28°. The angle $\theta 2$ between the second inclined surface 7 and the axis of the leg portion 3 is greater than the angle $\theta 1$, and is preferably in the range between 32° and 50°, and for example, 48°. The second inclined surface 7 intersects the semi-cylindrical peripheral surface of the leg portion 3 facing the opposite leg portion 3, so that this intersection defines the distal end edge 8 of the leg portion 3.

A number of the above surgical staples 1 are loaded or charged into a stapler in juxtaposed relation to one another. The central portion of the base portion 2 of each staple 1 is engaged with an anvil 200 of the stapler, and in this condition the opposite end portions of the base 2 are urged respectively by a pair of projections 201a and 201a of a ram 201 of the stapler to be bent at an angle of substantially 90° with respect to the remainder of the base portion 2, so that the distal end edges 8 of the two leg portions 3 and 3 move toward each other. Thus, the staple 1 is deformed into a generally rectangular shape. During this deformation, the pair of leg portions 3 and 3 are caused to penetrate into the body of the patient on the opposite sides of the wound, thereby suturing or sewing up the wound.

As described above, the second inclined surface 7, having a relatively large angle with respect to the axis of the leg portion 3, is formed on the distal end portion of the leg portion 3. With this arrangement, the distal end portion of the leg portion 3 in the vicinity of the distal end edge 8 has an increased mechanical strength. Therefore, even when this distal end portion is subjected to a considerable impact, it will not be deformed, bent or broken. Further, the second inclined surface 7 is continuous with the first inclined surface 6 having a smaller inclination angle than that of the second inclined surface 7. Therefore, when the leg portion 3 is to be caused to penetrate into the flesh of the patient, there is encountered a relatively small resistance to such penetration, thus achieving a good penetrating ability of the leg portion 3.

When the surgical staple 1 is viewed from the side thereof (FIG. 11), each leg portion 3 extends straight throughout the entire length thereof, that is, up to its distal end. Also, as seen from FIG. 10, the distal end edge 8 is not rounded when viewed from the front side of the staple 1. These features are achieved by moving the cutting edge 32b of each blade member 32 toward the leg portion 3 in inclined relation to the axis of the leg portion 3 and then by shearing the leg portion 3. These features improve the penetrating ability of the leg portion 3.

With the above-mentioned shearing method, burrs will not be formed on the distal end edge 8. The reason for this is not clear, but it is thought that this is because the rupture of the leg portion 3 occurring during the shearing operation is not influenced by a clearance between the the blade member 32 and its mating receptive member 42. Since no burr is formed on the distal end edge 8, the flesh of the patient is not damaged unnecessarily when each leg portion 3 is caused to penetrate the flesh.

While the present invention has been specifically shown and described herein, the invention itself is not to be restricted to the exact showing of the drawings and the description thereof, and various modifications can be made without departing from the spirit of the invention.

What is claimed is:

1. A surgical staple comprising a body having an elongated base portion and a pair of leg portions extending respectively from opposite ends of said base portion in intersecting relation to said base portion, each of said leg portions having a pair of first and second inclined surfaces at an outer periphery of a distal end portion of said leg portion remote from said base portion, said first and second inclined surfaces being inclined with respect to the axis of said leg portion, said first inclined surface being disposed intermediate the opposite ends of said leg portion, said second inclined surface extending between said first inclined surface and the distal end of said leg portion, the angle of said first inclined surface with respect to the axis of said leg portion being smaller than the angle of said second inclined surface with respect to the axis of said leg portion, said second inclined surface intersecting the outer peripheral surface of said leg portion at the distal end of said leg portion to form a sharp distal end edge.

2. A surgical staple according to claim 1, in which the angle of said first inclined surface with respect to the axis of said leg portion is in the range of between 20° and 30°, the angle of said second inclined surface with respect to the axis of said leg portion being in the range of between 32° and 50°.

3. A surgical staple according to claim 1, in which the axis of said base portion and the axes of the pair of leg portions are disposed in a common plane, said first and second inclined surfaces being disposed perpendicularly to said common plane, and said first and second inclined surfaces on each leg portion facing away from the opposite leg portion.

4. A surgical staple according to claim 1, in which said body has a substantially circular cross-section, said base portion being straight, said pair of leg portions being disposed parallel to each other and disposed perpendicularly to said base portion.

* * * * *